(12) United States Patent
Nakazawa et al.

(10) Patent No.: US 9,927,378 B2
(45) Date of Patent: Mar. 27, 2018

(54) ON-LINE COATING ADHESION DETERMINATION APPARATUS OF GALVANNEALED STEEL SHEET, AND GALVANNEALED STEEL SHEET MANUFACTURING LINE

(71) Applicant: NIPPON STEEL & SUMITOMO METAL CORPORATION, Tokyo (JP)

(72) Inventors: Makoto Nakazawa, Chiba (JP); Hajime Fujimura, Osaka (JP); Shohei Aoyama, Tokai (JP); Koichiro Sano, Tokyo (JP); Masaaki Omodaka, Obu (JP); Shigeru Hashimoto, Kimitsu (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 135 days.

(21) Appl. No.: 15/030,737

(22) PCT Filed: Oct. 25, 2013

(86) PCT No.: PCT/JP2013/079044
§ 371 (c)(1),
(2) Date: Apr. 20, 2016

(87) PCT Pub. No.: WO2015/059835
PCT Pub. Date: Apr. 30, 2015

(65) Prior Publication Data
US 2016/0252469 A1 Sep. 1, 2016

(51) Int. Cl.
*G01N 23/00* (2006.01)
*G01N 23/207* (2018.01)

(52) U.S. Cl.
CPC ..... *G01N 23/207* (2013.01); *G01N 2223/624* (2013.01); *G01N 2223/633* (2013.01); *G01N 2223/643* (2013.01)

(58) Field of Classification Search
CPC ................. G01N 2223/624; G01N 23/207
See application file for complete search history.

(56) References Cited

U.S. PATENT DOCUMENTS

| 4,064,437 A | 12/1977 | Hirose et al. |
| 5,155,751 A | 10/1992 | Chohata et al. |
(Continued)

FOREIGN PATENT DOCUMENTS

| CN | 1392956 A | 1/2003 |
| CN | 1800839 A | 7/2006 |
(Continued)

OTHER PUBLICATIONS

Extended European Search Report dated Apr. 25, 2017, issued in European Patent Application No. 13896032.3.
(Continued)

*Primary Examiner* — Dani Fox
(74) *Attorney, Agent, or Firm* — Birch, Stewart, Kolasch & Birch, LLP

(57) ABSTRACT

An on-line coating adhesion determination apparatus of a galvannealed steel sheet, includes: an X-ray tube which irradiates a galvannealed steel sheet that travels on a transportation line, with X-rays; an optical system which allows the X-rays emitted from the X-ray tube to irradiate the galvannealed steel sheet as a parallel beam and be diffracted; and a detector which measures the intensity of the diffracted X-rays and is installed at a position at which the X-ray diffraction peak corresponding to a crystal lattice spacing d of 1.5 Å or higher is detected, in which an emitted beam luminance of the X-rays is 20 W/mm² or higher, and the width-direction gain of the X-rays in the optical system is 0.15 or higher. The crystal lattice spacing d may be 1.914 Å.

(Continued)

In addition, the energy of the incident X-rays from the X-ray tube may be lower than the excitation energy of Fe-Kα fluorescence X-ray.

7 Claims, 9 Drawing Sheets

(56) References Cited

U.S. PATENT DOCUMENTS

| | | | |
|---|---|---|---|
| 5,414,747 | A | 5/1995 | Ruud et al. |
| 2002/0003858 | A1 | 1/2002 | Kondo et al. |
| 2002/0174918 | A1 | 11/2002 | Fujimura et al. |
| 2006/0140343 | A1 | 6/2006 | Gibson et al. |
| 2007/0058776 | A1 | 3/2007 | Kataoka et al. |
| 2008/0117511 | A1 | 5/2008 | Chen |
| 2012/0288058 | A1 | 11/2012 | Maeyama et al. |

FOREIGN PATENT DOCUMENTS

| | | | |
|---|---|---|---|
| CN | 201251557 | Y | 6/2009 |
| CN | 101558454 | A | 10/2009 |
| EP | 0 473 154 | A2 | 3/1992 |
| EP | 1 233 265 | A1 | 8/2002 |
| EP | 2 395 128 | A1 | 12/2011 |
| JP | 52-21887 | A | 2/1977 |
| JP | 56-94249 | A | 7/1981 |
| JP | 58-190747 | A | 11/1983 |
| JP | 60-58537 | A | 4/1985 |
| JP | 62-59844 | A | 3/1987 |
| JP | 1-301155 | A | 12/1989 |
| JP | 3-249162 | A | 11/1991 |
| JP | 4-42044 | A | 2/1992 |
| JP | 4-110644 | A | 4/1992 |
| JP | 5-45305 | A | 2/1993 |
| JP | 5-264477 | A | 10/1993 |
| JP | 6-347247 | A | 12/1994 |
| JP | 7-260715 | A | 10/1995 |
| JP | 9-33455 | A | 2/1997 |
| JP | 2001-272358 | A | 10/2001 |
| JP | 2002-168811 | A | 6/2002 |
| JP | 3329931 | B2 | 9/2002 |
| JP | 2010-121198 | A | 6/2010 |
| JP | 2010-265525 | A | 11/2010 |
| JP | 2012-255769 | A | 12/2012 |
| KR | 10-1992-0004832 | A | 3/1992 |
| KR | 10-2006-0071739 | A | 6/2006 |
| KR | 10-2007-0031231 | A | 3/2007 |
| KR | 10-2009-0071208 | A | 7/2009 |

OTHER PUBLICATIONS

European Search Report for EP 13781069 dated Nov. 4, 2015.
Fujinawa et al., "Development of a High-Resolution and High-Accuracy Parallel Beam Powder Diffractometer Using Laboratory X-Ray Sources", Advances in X-Ray Chemical Analysis, Japan 31, pp. 11-27, issued in 2000 by AGNE Gijutsu Center Inc., total 19 pages.
Harada, "New X-ray Source based on Multilayer Mirror", Structural Object, vol. 10, No. 1, pp. 20-29, issued in 2004 by AGNE Gijutsu Center Inc.
International Preliminary Report on patentability for PCT/JP2013/079044 (PCT/IPEA/409) dated Oct. 26, 2015.
International Search Report for PCT/JP2013/062170 dated Jun. 25, 2013.
International Search Report for PCT/JP2013/079044 dated Jan. 14, 2014.
Kawabe et al., "Continuous Measurement of Fe Content in Galvannealed Coating", Kawasaki Steel Technical Report, 18 (1986) 2, pp. 129-135, total 15 pages.
Notice of Allowance for KR 10-2014-7000382 dated Aug. 28, 2015.
Office Action for CN 201380002155.2 dated Aug. 5, 2015.
Office Action for U.S. Appl. No. 14/380,441 dated Dec. 31, 2015.
Taniyama et al., "In-situ Observation of Growth Behavior of Fe-Zn Intermetallic Compounds at Initial Stage of Galvannealing Process", Materials Transactions, vol. 45, No. 7, Jan. 1, 2004, pp. 2326-2331.
Written Opinion of the International Searching Authority for PCT/JP2013/079044 (PCT/ISA/237) dated Jan. 14, 2014.
Chinese Office Action dated Dec. 13, 2017, issued in Chinese Application No. 201380080399.2.

$\Delta = 2\tan^{-1}(t/L)$

ON-LINE COATING ADHESION DETERMINATION APPARATUS OF GALVANNEALED STEEL SHEET, AND GALVANNEALED STEEL SHEET MANUFACTURING LINE

TECHNICAL FIELD OF THE INVENTION

The present invention relates to an on-line coating adhesion determination apparatus of a galvannealed steel sheet, and a galvannealed steel sheet manufacturing line.

RELATED ART

A galvannealed steel sheet has been used worldwide as a steel sheet for vehicles. The quality characteristics required for the galvannealed steel sheet include corrosion resistance, coating properties, weldability, powdering resistance during press forming, and Hacking resistance during press forming, and the like. Fe—Zn phases constituting the coating layer of the galvannealed steel sheet include a $\zeta$ phase, a $\delta_1$ phase, and a $\Gamma \cdot \Gamma_1$ phase. Among the above-described characteristics, press formability particularly represented by powdering resistance and flaking resistance is dependent on the amounts of the $\zeta$ phase and the $\Gamma \cdot \Gamma_1$ phase. The powdering resistance is enhanced as the $\Gamma \cdot \Gamma_1$ phase is reduced, and the flaking resistance is enhanced as the $\zeta$ phase is reduced. Therefore, in order to obtain good press formability, a coating layer mainly containing the $\delta_1$ phase is required.

In order to form the coating layer mainly containing the $\delta_1$ phase, the coating bath composition (Al concentration in a bath), the bath temperature of a coating bath, and heating and cooling conditions for alloying need to be optimized depending on the steel components. Typically, the Al concentration in a bath and the bath temperature are maintained in constant ranges, and moreover, a heating and cooling pattern that is considered to be optimal is determined depending on an alloying rate of the steel for the operation. However, in practice, due to operational conditions in an upstream process (a process before coating) such as hot rolling, the alloying rate may vary in coils even in same type of steel and in parts even in same coil depending on actual operational conditions. Therefore, each time, an operator finely adjusts the heating and cooling conditions while visually checking the degree of alloying. As a result, which alloy phase is obtained and whether or not powdering resistance and flaking resistance are good are checked by off-line testing and analysis on the representative parts (typically a front portion and/or a tale portion) of a coil after production.

However, in the method of checking coating quality through the off-line testing and analysis, quick feedback of the operational condition may not be achieved. Therefore, for example, in a case where an alloying rate is changed due to a change in steel type, there is a risk of a reduction in yield. In addition, for example, depending on coiling conditions during hot rolling or the like, there may be cases where alloying of the front portion of a coil is slower than alloying of the middle portion. In this case, when the operation is performed to meet the alloying condition of the front portion, the middle portion is excessively alloyed, and powdering of most of parts of the coil may become apparent.

In order to prevent the problems beforehand, on-line measurement with high accuracy over the entire length of the coil is effective. A technique employed for this purpose is an on-line X-ray diffraction method. An X-ray diffraction method is a method for qualitative and quantitative measurement of crystal phases in a coating layer using the diffraction phenomenon which occurs when crystals are irradiated with X-rays. In a case where this method is used for the on-line measurement, selecting diffracted X-rays having a good correlation between the diffracted X-ray intensity and the crystal phase thickness is necessary. Furthermore, in order to obtain high measurement accuracy, selecting diffracted X-rays having a high intensity from a practical diffraction angle range is necessary.

In Patent Documents 1 and 2, as a practical diffraction angle ($2\theta$) range, $2\theta > 80°$ (in a case where Cr is used as an X-ray target, a crystal lattice spacing is d<1.78 Å) is disclosed as a range in which effects of flapping of a steel sheet, the thermal effect of the steel sheet, and a change in incident X-ray intensity are small. As the crystal lattice spacing which satisfies the above conditions, those that are widely used in the past are, for example, as described in Patent Documents 2 to 5, d=1.26 Å ($2\theta=130°$ when the target is Cr) for a $\zeta$ phase, d=1.28 Å ($2\theta=127°$ when the target is Cr) for a $\delta_1$ phase, and d=1.22 Å ($2\theta=139°$ when the target is Cr) for a $\Gamma \cdot \Gamma_1$ phase.

However, it cannot be said that the on-line X-ray diffraction method according to the related art is sufficient to perform on-line measurement over the entire coil length with high accuracy, to quickly feed the results back to operational conditions, and to prevent excessive alloying or non-alloying beforehand. The biggest reason is that the three X-ray diffraction peaks respectively indicated by the $\zeta$ phase, the $\delta_1$ phase, and the $\Gamma \cdot \Gamma_1$ phase, which have been used in the past, are adjacent to each other and are present in a region with a background that is high and is not flat. In the related art, a constraint condition of $2\theta > 80°$ which is a range in which the effects of the flapping of a steel sheet, the thermal effect from the steel sheet, and a change in incident X-ray intensity are small, and a condition of simultaneous measurement caused by the fact that the X-ray diffraction peaks of the three phases (the $\zeta$ phase, the $\delta_1$ phase, and the $\Gamma \cdot \Gamma_1$ phase) are adjacent, are considered to be important. As a result, the technique is extremely insufficient for achieving the original object to measure the thickness of each phase with good accuracy.

In addition, in recent years, for the enhancement in the productivity of a manufacturing line or competitiveness, the manufacturing line of the galvannealed steel sheet has been increased in speed. In order to determine the coating adhesion of the galvannealed steel sheet in a high-speed manufacturing line on-line, an analysis time for the determination of the coating adhesion needs to be reduced. In order to significantly determine the difference between a steel sheet having good coating adhesion and a steel sheet having poor coating adhesion, a significant difference of three times ($3\sigma$) or more of measurement variation needs to be provided between the measurement values of the two.

As the analysis time for the determination is increased, the length of the steel sheet that has passed from the start to the end of the determination is increased. When the manufacturing line is increased in speed, the necessary steel sheet length for the determination is further increased. When the length is excessively increased, quality assurance on the entire length of the coil becomes difficult, and rapid feedback to the operational conditions becomes difficult. In order to enable measurement within a shorter time, the improvement in the signal intensity and the S/N ratio is necessary. In addition, steel sheet vibrations are increased due to an increase in speed, and there is a greater need for reducing the effect of the steel sheet vibrations on signals than in the related art.

Patent Document 6 discloses a technique for reducing an effect of steel sheet vibrations. In Patent Document 6, an incident X-ray beam is incident on a multi-layer film mirror to be collimated. As a result, diffracted X-rays generated by irradiating the coating layer of a steel sheet surface with the incident X-ray beam are collimated. Therefore, even in a case where the distance between the diffraction position of the X-rays and a detection system is changed due to vibrations of the steel sheet, there is an advantage in that the detected intensity of the diffracted X-rays is stabilized.

The effect of the multi-layer film mirror is also described in Non-Patent Document 1. An example, in which a multi-layer film mirror and a parallel slit are used in order to efficiently collimate divergent beams emitted from an X-ray source in a laboratory, is disclosed.

PRIOR ART DOCUMENT

Patent Document

[Patent Document 1] Japanese Unexamined Patent Application, First Publication No. S52-21887
[Patent Document 2] Japanese Unexamined Patent Application, First Publication No. H05-45305
[Patent Document 3] Japanese Unexamined Patent Application, First Publication No. H09-33455
[Patent Document 4] Japanese Unexamined Patent Application, First Publication No. H07-260715
[Patent Document 5] Japanese Unexamined Patent Application, First Publication No. H04-110644
[Patent Document 6] Japanese Unexamined Patent Application, First Publication No. 2002-168811

Non-Patent Document

[Non-Patent Document 1] "Advances in X-Ray Analysis 31", P11 to 27, issued in 2000 by AGNE Gijutsu Center Inc.

DISCLOSURE OF THE INVENTION

Problems to be Solved by the Invention

The present invention has been made taking the foregoing problems into consideration, and an object thereof is to provide an on-line coating adhesion determination apparatus of a galvannealed steel sheet, which can follow a further increase in the speed of a manufacturing line, and a galvannealed steel sheet manufacturing line.

Means for Solving the Problem

The present inventors had intensively and repeatedly conducted research focusing on the fact that a background intensity is low and flat (is approximately horizontal) in a range in which a diffraction angle $2\theta$ is on a low angle side. As a result, it was found that on a low angle side corresponding to a crystal lattice spacing d of 1.5 Å or higher, a plurality of X-ray diffraction peaks for a single phase are present. The inventors had repeatedly examined the quantitativeness of the peak intensities, and as a result, identified a peak for each phase, which has excellent quantitativeness and has low background intensity. Moreover, it was found that, by using a value obtained by subtracting a background intensity from the intensity of X-ray diffraction peak corresponding to a crystal lattice spacing d of 1.914 Å, the thickness of a $\Gamma \cdot \Gamma_1$ phase, which affects the coating adhesion of a galvannealed steel sheet, can be measured with good accuracy.

Subsequently, the present inventors proceeded to examine the realization of the technique. In order to apply the technique to a manufacturing line having high sheet threading speed for the steel sheet, problems of steel sheet vibrations during sheet threading need to be solved. Under the thought that a parallel beam optical system has to be used as an optical system in order to reduce the effect of steel sheet vibrations, a method of detecting a Fe—Zn phase low angle peak corresponding to a crystal lattice spacing d of 1.5 Å or higher, in the parallel beam optical system with high sensitivity was intensively and repeatedly examined. As a result, first, regarding the specifications of an X-ray tube, selection of an output, a focal size, an extraction angle, and an extraction method is important for sensitivity enhancement. Next, the specifications of an optical system for irradiating a sample with a beam emitted from the X-ray tube and efficiently guiding the beam to a detector were examined. As a result, it was found that the detection efficiency particularly in an incidence optical system can be enhanced by appropriately setting a capture angle and reflectance. Here, the present inventors repeatedly conducted a systematic experiment by changing such parameters, and as a result, found that on the premise of a parallel beam optical system, a desired diffraction peak can be detected with good sensitivity by designing a X-ray tube and the optical system so as to allow two parameters including "emitted beam luminance" and "width-direction gain" to be higher than specific lower limits. Therefore, the present inventors produced an on-line X-ray diffraction apparatus which satisfied the above conditions and installed the apparatus at a position at which the sum of a sheet thickness change and steel sheet vibrations was within ±3 mm between an alloying furnace and coiling in a continuous galvanizing line. The present inventors found that on-line adhesion determination of a galvannealed sheet can be actually performed with good accuracy within a short period of time and completed the present invention.

The present invention has been made on the basis of the findings, and the gist is as follows:

(1) That is, according to an aspect of the present invention, an on-line coating adhesion determination apparatus of a galvannealed steel sheet, includes: an X-ray tube which irradiates a galvannealed steel sheet that travels on a transportation line, with X-rays; an optical system which allows the X-rays emitted from the X-ray tube to irradiate the galvannealed steel sheet as a parallel beam and be diffracted; and a detector which measures an intensity of the diffracted X-rays and is installed at a position at which the X-ray diffraction peak corresponding to a crystal lattice spacing d of 1.5 Å or higher is detected, in which an emitted beam luminance of the X-rays is 20 W/mm² or higher, and the width-direction gain of the X-rays in the optical system is 0.15 or higher.

(2) In the on-line coating adhesion determination apparatus of a galvannealed steel sheet described in (1), the detector may be installed at a position of a diffraction angle at which the X-ray diffraction peak corresponding to a crystal lattice spacing d of 1.914 Å is detected.

(3) In the on-line coating adhesion determination apparatus of a galvannealed steel sheet described in (1) or (2), as the X-ray tube, an X-ray tube in which an energy of the X-rays incident on the galvannealed steel sheet is lower than an excitation energy of Fe-Ku fluorescence X-rays, may be used.

(4) According to another aspect of the present invention, a galvannealed steel sheet manufacturing line includes: installing the on-line coating adhesion determination apparatus described in any one of (1) to (3), at a position at which the sum of the sheet thickness change and steel sheet vibrations is within ±3 mm between an alloying furnace and coiling.

Effects of the Invention

By applying the on-line coating adhesion determination apparatus of a galvannealed steel sheet of the present invention, determination of good adhesion and poor adhesion can be achieved within a short period time. Therefore, even when the sheet threading speed of a steel sheet in a manufacturing line is further increased, on-line measurement can be performed over the entire length of a coil with good accuracy. In addition, by quickly feeding the results back to operational conditions, excessive alloying or non-alloying can be prevented beforehand. As a result, this significantly contributes to improvement of yield and quality assurance even during high-speed sheet threading. Therefore, a galvannealed steel sheet with excellent coating quality can be stably supplied to customers at low cost.

EMBODIMENTS OF THE INVENTION

Figure 1:
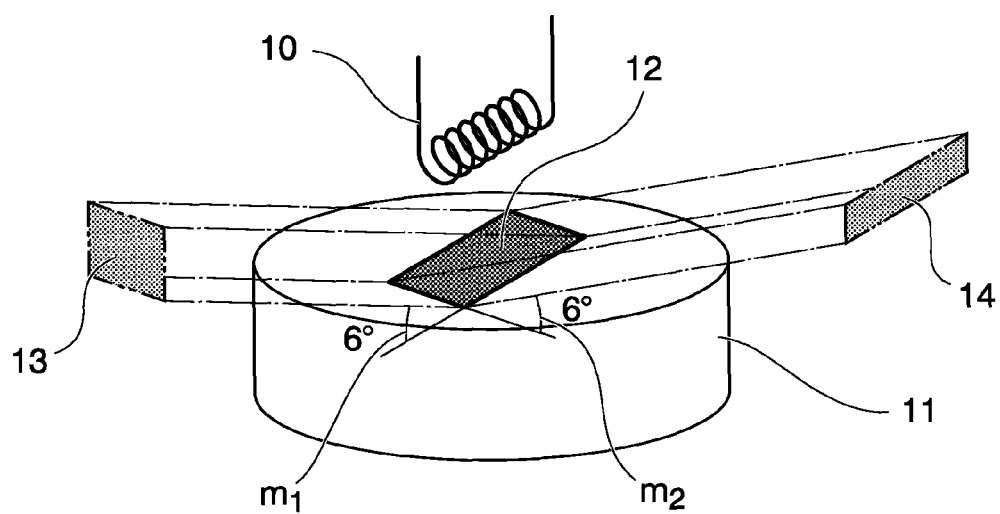
FIG. 1 is a schematic view showing a focal size, an extraction angle, an extraction method, and an actual focal size of an X-ray tube in an on-line coating adhesion determination apparatus according to an embodiment of the present invention.

Hereinafter, an on-line coating adhesion determination apparatus of a galvannealed steel sheet according to an embodiment of the present invention (hereinafter, sometimes simply referred to as a determination apparatus according to this embodiment), and a galvannealed steel sheet manufacturing line in which the apparatus according to the embodiment of the present invention is installed and a high-speed operation is enabled (hereinafter, sometimes simply referred to as a manufacturing line according to this embodiment) will be described in detail with reference to the drawings.

The determination apparatus according to this embodiment is a measurement apparatus which measures the thickness of a predetermined phase contained in an Fe—Zn alloy phase of the galvannealed steel sheet, and includes an X-ray tube which irradiates the galvannealed steel sheet with X-rays, an optical system from the X-ray tube to a detector, and the detector which measures the intensity of diffracted X-rays obtained through the X-ray irradiation. Using a parallel beam optical system as the optical system, X-rays are allowed to be incident on the galvannealed steel sheet and be diffracted. In addition, the detector is installed at a position corresponding to a diffraction angle at which X-rays diffraction peak corresponding to a crystal lattice spacing d of 1.5 Å or higher are detected. In addition, the emitted beam luminance of the X-rays is 20 W/mm$^2$ or higher, and the width-direction gain of the X-rays in the optical system is 0.15 or higher.

Hereinafter, an X-ray diffraction method applied to the determination apparatus according to this embodiment will be described. The X-ray diffraction method applied to the determination apparatus according to this embodiment includes irradiating a polycrystalline sample with characteristic X-rays and measuring the reflection intensity at a specific diffraction angle and is classified into the Debye-Scherrer method. In addition, an X-ray diffraction apparatus which can be applied to the determination apparatus according to this embodiment is constituted by an X-ray tube which generates an X-ray beam, various slits for restricting the divergence of the X-ray beam, a detector, a light-receiving slit, a count recording device, and the like.

The X-ray tube which can be used in this embodiment generates thermal electrons by allowing current to flow through a filament, generates X-rays by allowing the thermal electrons to accelerate at a high voltage of tens of kilo voltages and strike a metal target, and extract the generated X-rays through a beryllium window. The metal target of the X-ray tube is selected in consideration of absorption of X-rays by a specimen and measurement accuracy, and Cu, Cr, Fe, Co, Mo, W and the like are used. Among these, Cu, Cr, and Co are particularly preferable due to excellent versatility. The generated X-rays include, as well as Kα rays as an object, Kβ rays and white X-ray components and thus need to be converted into monochromic light by removing such components. Conversion of the X-ray beam into monochromic light is performed by inserting a Kβ filter made of a metallic foil in front of the light-receiving slit or by using a monochromator. Further, a pulse height analyzer may also be combined or a collimation system using an X-ray collimator may also be employed.

As the slit for restricting the divergence of the X-ray beam, a solar slit for restricting the divergence of the X-ray beam in a vertical direction and a divergence slit for restricting the angle of divergence of a sample in a horizontal plane is preferably used. Diffracted X-rays generated by irradiating a material surface with the X-ray beam are collected via the light-receiving slit, and are detected by the X-ray detector further via the solar slit and a scattering slit such that the intensity thereof is measured.

Next, this embodiment will be described in more detail.

First, the X-ray tube used in the on-line coating adhesion determination apparatus of the galvannealed steel sheet according to this embodiment will be described. As the X-ray tube, a sealed-type X-ray tube is preferably used. As the X-ray source, as well as the X-ray tube, there is a rotating anticathode-type X-ray generating device, which is advantageous in terms of high output. However, in a case of being used in the galvannealed steel sheet manufacturing line, maintenance and management of a vacuum system and the like are complex. Therefore, the X-ray tube is appropriate. As the sealed-type X-ray tube, any of a fluorescence X-ray tube and a diffracted X-ray tube may be used. However, the diffracted X-ray tube which has a small focal size and high luminance is more appropriate. Examples of the sealed-type X-ray tube are shown in Table 1. The fluorescence X-ray tube has a relatively greater focal size than that of the diffracted X-ray tube, and tubes of Nos. 1 to 3 in Table 1 correspond to the fluorescence X-ray tube. Tubes of Nos. 4 to 15 in Table 1 correspond to the diffracted X-ray tube. In addition, a focal point luminance in Table 1 is a value obtained by dividing an output (W) by the area (mm$^2$) of a focal point.

TABLE 1

| | Fluorescence/Diffraction | X-ray source | Focal size (mm × mm) | Output (kW) | Focal point luminance W/mm$^2$ |
|---|---|---|---|---|---|
| 1 | Fluorescence | Mo/W | 7 × 7.5 | 3 | 57 |
| 2 | Fluorescence | Cr | 7 × 7.5 | 3 | 57 |
| 3 | Fluorescence | Rh | φ14 | 3 | 19 |
| 4 | Diffraction | Cr | 0.4 × 12 | 1.9 | 396 |
| 5 | Diffraction | Cr | 1 × 10 | 1.8 | 180 |
| 6 | Diffraction | Cr | 0.4 × 8 | 1.3 | 406 |
| 7 | Diffraction | Cr | 2 × 12 | 2.7 | 113 |
| 8 | Diffraction | Cu | 0.4 × 12 | 2.2 | 458 |
| 9 | Diffraction | Cu | 1 × 10 | 2 | 200 |
| 10 | Diffraction | Cu | 0.4 × 8 | 1.5 | 469 |
| 11 | Diffraction | Cu | 2 × 12 | 2.7 | 113 |
| 12 | Diffraction | Co | 0.4 × 12 | 1.8 | 375 |
| 13 | Diffraction | Co | 1 × 10 | 1.8 | 180 |
| 14 | Diffraction | Co | 0.4 × 8 | 1.2 | 375 |
| 15 | Diffraction | Co | 2 × 12 | 2.7 | 113 |

Regarding the specifications of the X-ray tube according to this embodiment, in addition to an output, selection of a focal size, an extraction angle, and an extraction method is important for sensitivity enhancement. FIG. 1 shows the relationship between the focal size, the extraction angle, the extraction method, the actual focal size after extraction in the diffracted X-ray tube. As shown in FIG. 1, inside the X-ray tube, a filament 10, and a metal target 11 disposed to be separated from the filament 10 are provided. By allowing current to flow through the filament 10, thermal electrons are generated, and the generated thermal electrons are allowed to strike the metal target 11, thereby generating X-rays. A focal point 12, which is a region struck by the thermal electron, is formed on the metal target 11. The shape of the focal point 12 is a shape close to a projected shape of the filament 10 on the metal target 11, and in the example shown in FIG. 1, is a substantially rectangular shape having a width of a (mm) in a lateral direction, and a length of b (mm) in a longitudinal direction. When a perpendicular line is drawn from the filament 10 to the metal target 11, extraction angles $m_1$ and $m_2$ are approximately 6° with respect to a plane perpendicular to the perpendicular line.

Regarding the inclination direction of the extraction angles $m_1$ and $m_2$, as shown in FIG. 1, the inclination direction may be set along the width direction of the focal point 12, and the inclination direction may be set along the longitudinal direction thereof. The extraction method includes "point extraction" in which the cross-sectional shape of the X-ray beam is close to a square shape, and "line extraction" in which the cross-sectional shape of the extracted beam is a line shape, according to the inclination direction of the target. The actual focal size varies depending on the selection of the extraction method. Here, the actual focal point refers to the cross-sectional size of the X-ray beam immediately after being emitted toward the outside of the X-ray tube.

In a case where the size (expressed as width×length, the same is applied hereinafter) of the focal point 12 in a plan view is a (mm)×b (mm), when the point extraction is employed, as shown in FIG. 1, the extraction direction of the X-rays is inclined at the extraction angle $m_1$ along the longitudinal direction of the focal point. Therefore, the dimensions of the focal size in the longitudinal direction are compressed, and an actual focal size 13 after the extraction becomes a (mm)×tan ($m_1$)·b (mm). On the other hand, when the line extraction is employed, as shown in FIG. 1, the extraction direction of the X-rays is inclined at the extraction angle $m_2$ along the width direction of the focal point. Therefore, the dimensions of the focal size in the width direction are compressed, and the actual focal size 14 after the extraction becomes tan ($m_2$)·a (mm)×b (mm). For example, when the size of the focal point 12 in FIG. 1 is set to 1 (mm)×10 (mm) and the extraction angle is set to 6°, the actual focal size 13 after the point extraction becomes 1 (mm)×1 (mm), and the actual focal size 14 after the line extraction becomes 0.1 (mm)×10 (mm).

Figure 2:
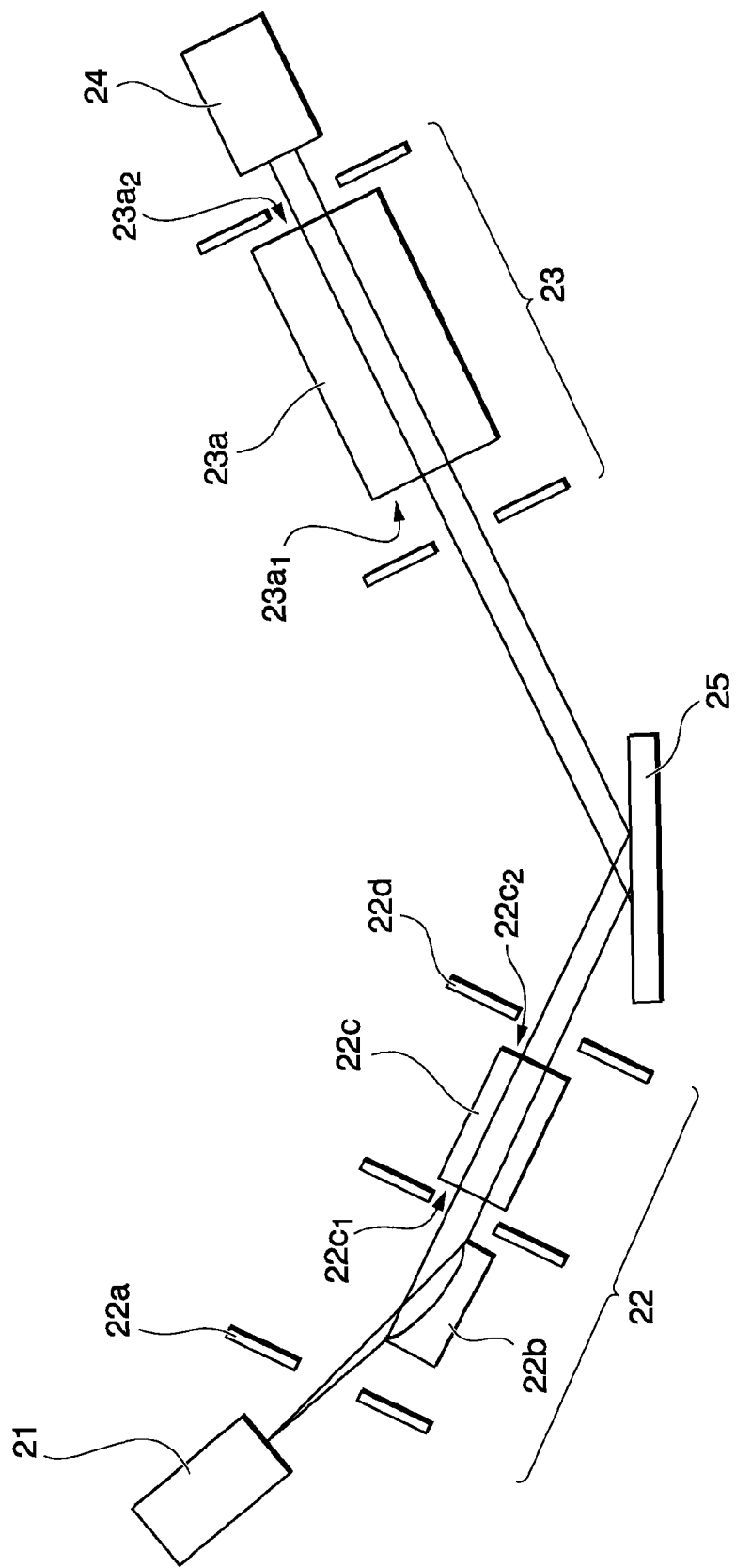
FIG. 2 is a schematic view showing main parts of the on-line coating adhesion determination apparatus according to the embodiment of the present invention.

Next, the optical system in the determination apparatus according to this embodiment will be described. In the determination apparatus according to this embodiment, a parallel beam optical system which is less likely to be affected by steel sheet vibrations during on-line measurement is used. FIG. 2 shows the overall view of the parallel beam optical system. The optical system of the determination apparatus according to this embodiment is constituted by an X-ray source 21, an incidence optical system 22, a light-receiving optical system 23, and a detector 24.

As the X-ray source 21 shown in FIG. 2, the above-described X-ray tube is used. In addition, in the incidence optical system 22, from the X-ray source 21 side, an emission slit 22a, a multi-layer film reflection mirror 22b in which the reflection surface has a parabolic cross-sectional outline shape, and an incidence side solar slit 22c are arranged in this order. In addition, in the solar slit 22c, an inlet side opening $22c_1$, which restricts the incidence expansion width of the X-rays incident to the solar slit 22c, and an outlet side opening $22c_2$, which restricts the emission expansion width of the X-rays emitted from the solar slit 22c, are provided. Furthermore, a restriction slit 22d is disposed between the solar slit 22c and a sample 25. In addition, in the determination apparatus according to this embodiment, the multi-layer film reflection mirror 22b may also be omitted. Otherwise, instead of the multi-layer film reflection mirror 22b, an analyzing crystal may also be used. X-ray beam collimation is realized by the solar slit 22c alone, a combination of the multi-layer film reflection mirror 22b and the solar slit 22c, the analyzing crystal alone, a combination of the solar slit and the analyzing crystal, or the like.

An emission side solar slit 23a is disposed in the emission optical system 23. In addition, in the solar slit 23a, an inlet side opening $23a_1$, which restricts the incidence expansion width of the X-rays incident to the solar slit 23a, and an outlet side opening $23a_2$, which restricts the emission expansion width of the X-rays emitted from the solar slit 23a, are provided. In FIG. 2, reference numeral 25 denotes the galvannealed steel sheet, which becomes a sample for X-ray diffraction measurement. Hereinafter, the incidence optical system 22 and the light-receiving optical system 23 will be described in detail.

Figure 3A:
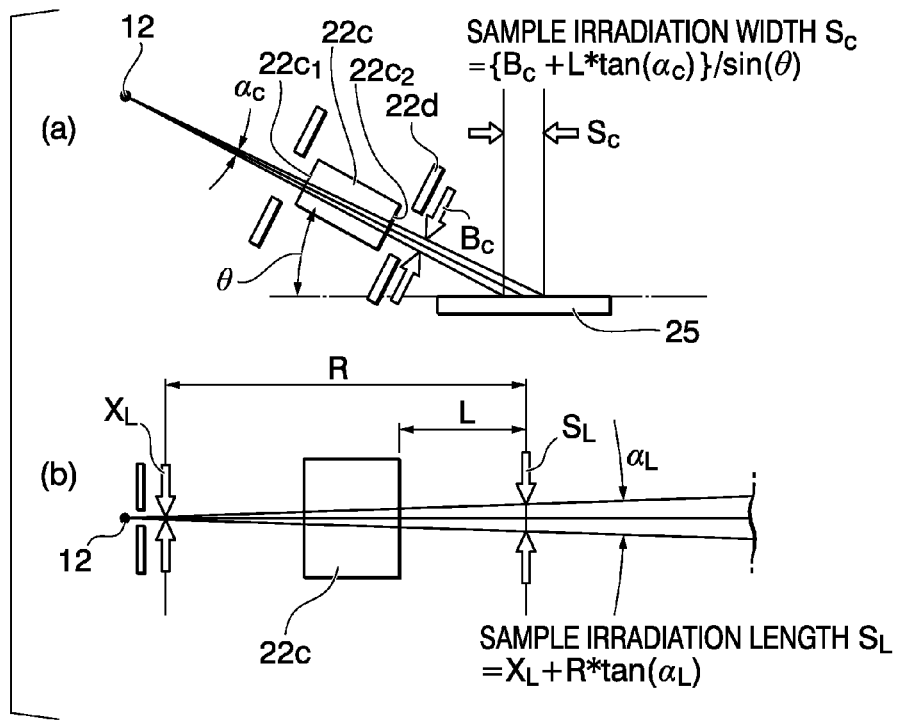
FIG. 3A is a view of the arrangement of an optical system on an incidence side in a case where solar slit is used, in which (a) is a side view, and (b) is a view of a beam surface.
Figure 3B:
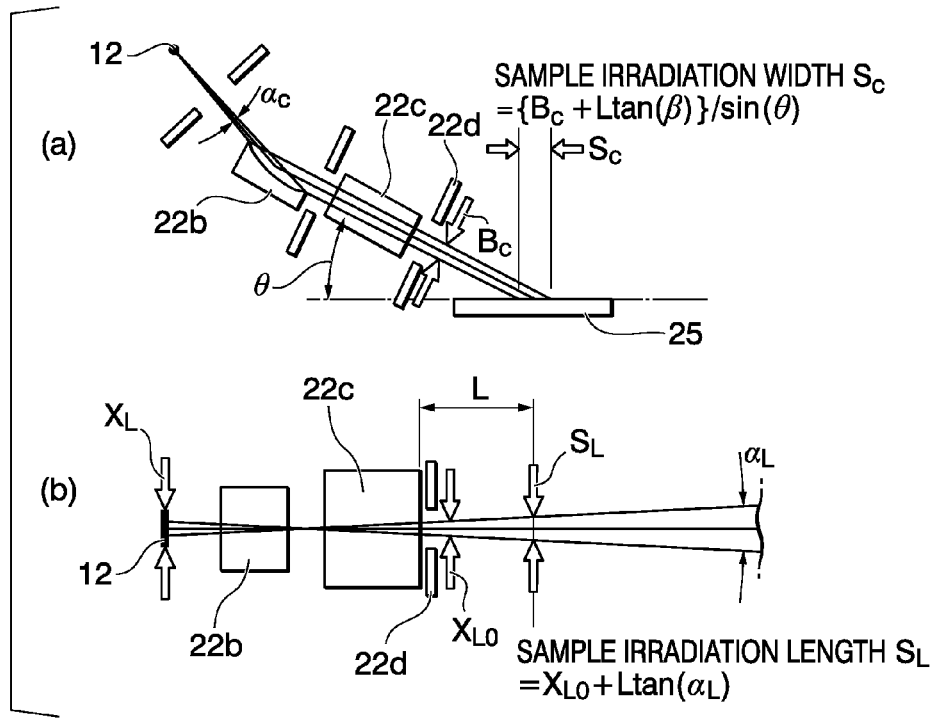
FIG. 3B is a view of the arrangement of the optical system on the incidence side in a case where a multi-layer film parabolic mirror and the solar slit are used, in which (a) is a side view, and (b) is a view of a beam surface.
Figure 5:
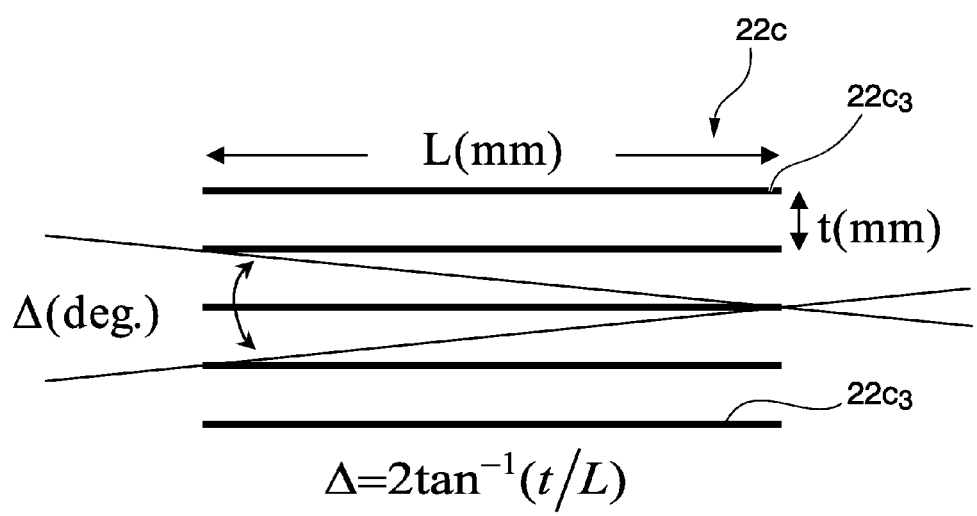
FIG. 5 a planar schematic view showing main parts of the solar slit.

A view of the arrangement of the incidence optical system 22 is shown in FIGS. 3A and 3B. FIG. 3A shows an example in which only the solar slit 22c is used as an optical element and X-rays subjected to the point extraction are incident thereon. (a) in FIG. 3A is a side view of the sample viewed from the side, and (b) in FIG. 3A is a view of a beam surface viewed vertically from above the sample (view of beam surface). The solar slit 22c is made by overlapping thin metal sheets at equal intervals, and is an optical element which restricts the divergence of incident X-rays and diffracted rays in the vertical direction in (a) in FIG. 3A. Regarding the X-rays generated from the focal point 12 in FIG. 1, the divergence of the incident X-rays in the vertical direction, that is, an overlap of Debye rings is limited by the solar slit 22c on the incidence side. Since X-rays are generated to expand and diverge in ring shapes, when a different ring-shaped X-ray distribution is present around an X-ray part to be used, diffracted rays may be shifted (umbrella effect). The divergence angle (Δ) of the solar slit 22c is determined by an interval (t) and a length (L) of a metal foil $22c_3$. The relationship is shown in FIG. 5. When the interval (t) of the metal foil $22c_3$ is narrow, the visual field of the incident X-rays in a height direction is limited, and thus the intensity is reduced. However, the divergence in the vertical direction is limited and the resolution is enhanced.

In this embodiment, by calculating the width (sample irradiation width) and length (sample irradiation length) of the X-rays irradiating the sample 25 and obtaining the emitted beam luminance on the sample 25, the specifications of the X-ray source 21 and the optical system are designed. First, a method of calculating the sample irradiation width and the sample irradiation length in a case where only the solar slit 22c is used as the optical element of the incidence optical system 22 and X-rays subjected to the point extraction are incident thereon will be described with reference to FIG. 3A. A sample irradiation width $S_c$ is calculated from an emitted beam width $B_c$, the distance from the outlet of the solar slit to the sample (hereinafter, referred to as sample distance) L, a capture angle width direction $\alpha_c$, and an X-ray incident angle θ with respect to the sample, by the following Expression (1).

$$S_c = (B_c + L \cdot \tan \alpha_c)/\sin \theta \qquad (1)$$

The emitted beam width $B_c$ is a value determined by the design of the optical element, and is approximately 1 mm. In FIG. 3A, the emitted beam width $B_c$ indicates the width of the X-ray beam passing through the outlet side opening $22c_2$ of the solar slit 22c. As a sample distance L is reduced, higher signal intensity is obtained. However, it is thought that the sample distance L is appropriately about 50 mm to 150 mm in consideration of use for on-line measurement of the galvannealed steel sheet.

The capture angle is an effective capture angle of a portion captured by the optical element from the X-rays that diverge in all directions from the focal point 12. As the capture angle is increased, the amount of X-rays captured by the optical element is increased. The capture angle width direction $\alpha_c$ is a capture angle when the optical system is viewed from the side. In the case where the solar slit 22c is used, the capture angle width direction $\alpha_c$ is an expansion angle of the X-ray beam passing through the solar slit 22c, and $\alpha_c$ is in a range of approximately 0.1° to 0.6°. The X-ray incident angle θ with respect to the sample 25 is typically set to about the half of the diffraction angle.

Next, as shown in (b) in FIG. 3A, the sample irradiation length $S_L$ is calculated from the actual focal length $X_L$ of the X-ray beam, a gonioradius R, and a capture angle longitudinal direction $\alpha_L$, by the following Expression (2).

$$S_L = X_L + R \cdot \tan \alpha_L \qquad (2)$$

The actual focal length $X_L$ is sectional lengths of the actual focal points 13 and 14 after the extraction shown in FIG. 1. The gonioradius R is the distance from the actual focal points 13 and 14 to the sample 25. The capture angle longitudinal direction $\alpha_L$ is a capture angle when the optical system is viewed from above the sample. In the case where the solar slit 22c is used, the capture angle longitudinal direction $\alpha_L$ is an expansion angle of the X-ray beam passing through the solar slit, and $\alpha_L$ is in a range of approximately 3° to 8°.

Figure 6:
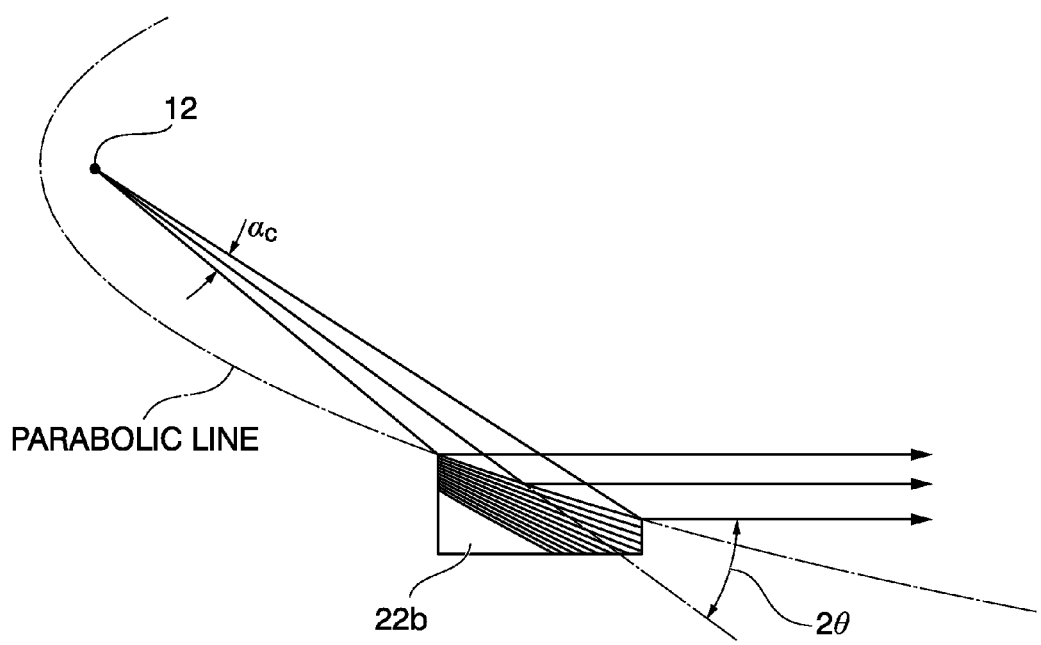
FIG. 6 is a side schematic view showing the function of the multi-layer film parabolic mirror.

Next, FIG. 3B is a view of the arrangement of the incidence optical system in a case where the solar slit 22c and the multi-layer film parabolic mirror 22b are used as the optical element and X-rays subjected to the line extraction are incident thereon. (a) in FIG. 3B is a side view of the sample viewed from the side, and (b) in FIG. 3B is a view of a beam surface viewed vertically from above the sample (view of beam surface). The multi-layer film parabolic mirror 22b is a lattice spacing inclination-type parabolic mirror, in which, as shown in FIG. 6, the mirror surface has a parabolic shape so as to allow the capture angle width direction $\alpha_c$ to be maximized and the lattice spacing is inclined to undergo Bragg reflection in parallel at any position of the shape. The details are described in Reference Document mentioned below. In a case where a multi-layer film mirror is used, the width direction represents a mirror surface longitudinal direction viewed from the X-ray source. The value of the capture angle width direction $\alpha_c$ of the multi-layer film parabolic mirror is in a range of appropriately 0.4 to 0.7. On the other hand, since the flat multi-layer film mirror has a constant lattice spacing, Bragg reflection conditions are determined. Therefore, the value of the capture angle width direction $\alpha_c$ of the flat multi-layer film mirror corresponds to a rocking curve width of the mirror, and this is also determined by the mirror design values and is in a range of approximately 0.05 to 0.10. The capture angle longitudinal direction $\alpha_L$ represents ray source capturing in the longitudinal direction in the optical system, and this is determined by the width of the outlet of the solar slit.
Reference Document: Structural Object Vol. 10, No. 1, P20 to 29, issued in 2004 by AGNE Gijutsu Center Inc.

A method of calculating the sample irradiation width and the sample irradiation length in a case where the multi-layer film parabolic mirror 22b in addition to the solar slit 22c are used as the optical element and X-rays subjected to the line extraction are incident thereon will be described with reference to FIG. 3B. The sample irradiation width $S_c$ is calculated from the emitted beam width $B_c$, the sample distance L, and the X-ray incident angle θ, by the following Expression (3).

$$S_c=(B_c+L\cdot\tan\beta)/\sin\theta \quad (3)$$

In Expression (3), β is an expansion angle of the emitted beam until the beam reaches the sample after being emitted from the solar slit 22c, and is a value determined by the design of the multi-layer film parabolic mirror 22b. In Examples of Table 3, 0.05° was used as a general value. $B_c$ is a value determined by the design of the optical element, and is approximately 1 mm. In FIG. 3B, $B_c$ indicates the width of the X-ray beam passing through the outlet side opening $22c_2$ of the solar slit 22c. L and θ are as described above with reference to FIG. 3A.

The sample irradiation length $S_L$ is calculated from a slit outlet focal length $X_{Lo}$, the sample distance L, and the capture angle longitudinal direction $\alpha_L$, by the following Expression (4).

$$S_L=X_{Lo}+L\cdot\tan\alpha_L \quad (4)$$

The slit outlet focal length $X_{Lo}$ becomes equal to the slit length of the restriction slit 22d in the case of the figure. The sample distance L and the capture angle longitudinal direction $\alpha_L$ are as described above.

The diffraction angle used in the determination apparatus according to this embodiment is an angle corresponding to a crystal lattice spacing d of 1.5 Å or higher. This is shown in Table 2. In addition, in this embodiment, the diffraction angle corresponding to the crystal lattice spacing d means that a range finely adjusted within ±0.5° is included. Particularly, in this embodiment, diffraction angles corresponding to the crystal lattice spacings d of Nos. 5, 7, 9, 10, 12, 13, and 15 are preferably employed. The diffraction angle is a preferable diffraction angle which enables a relatively high coefficient of correlation between the refraction intensity at each diffraction angle and the thickness of the alloy phase including the ζ phase, the $\delta_1$ phase, and the $\Gamma\cdot\Gamma_1$ phase and accurate measurement of adhesion of the coating layer.

TABLE 2

| No | Crystal lattice spacing d (Å) | Diffraction angle 2θ (°) Cr tube | Co tube | Cu tube | Fe—Zn alloy phase | Coefficient of correlation | Classification |
|---|---|---|---|---|---|---|---|
| 1 | 1.507 | 98.95 | 73.01 | 61.48 | ζ | 0.75 | Invention Examples |
| 2 | 1.536 | 96.45 | 71.42 | 60.20 | ζ | 0.72 | |
| 3 | 1.623 | 89.79 | 67.06 | 56.67 | $\delta_1$ | 0.58 | |
| 4 | 1.720 | 83.52 | 62.83 | 53.21 | ζ | 0.65 | |
| 5 | 1.833 | 77.35 | 58.56 | 49.70 | $\Gamma\cdot\Gamma_1$ | 0.90 | |
| 6 | 1.899 | 74.20 | 56.34 | 47.86 | ζ | 0.58 | |
| 7 | 1.914 | 73.49 | 55.86 | 47.47 | $\Gamma\cdot\Gamma_1$ | 0.94 | |
| 8 | 1.971 | 71.07 | 54.11 | 46.01 | $\Gamma\cdot\Gamma_1$ | 0.62 | |
| 9 | 2.363 | 57.97 | 44.59 | 38.05 | $\delta_1$ | 0.77 | |
| 10 | 2.593 | 52.43 | 40.45 | 34.56 | $\Gamma\cdot\Gamma_1$ | 0.90 | |
| 11 | 2.770 | 48.86 | 37.77 | 32.29 | ζ | 0.60 | |
| 12 | 3.692 | 36.15 | 28.11 | 24.09 | ζ | 0.86 | |
| 13 | 4.109 | 32.38 | 25.20 | 21.61 | ζ | 0.98 | |
| 14 | 5.535 | 23.89 | 18.64 | 16.00 | $\delta_1$ | 0.60 | |
| 15 | 6.351 | 20.78 | 16.23 | 13.92 | $\Gamma\cdot\Gamma_1$ | 0.71 | |
| 16 | 1.222 | 139.10 | 94.38 | 78.15 | $\Gamma\cdot\Gamma_1$ | — | Examples of related art |
| 17 | 1.279 | 127.08 | 89.01 | 74.06 | $\delta_1$ | — | |
| 18 | 1.260 | 130.66 | 90.72 | 75.37 | ζ | — | |

Figure 4:
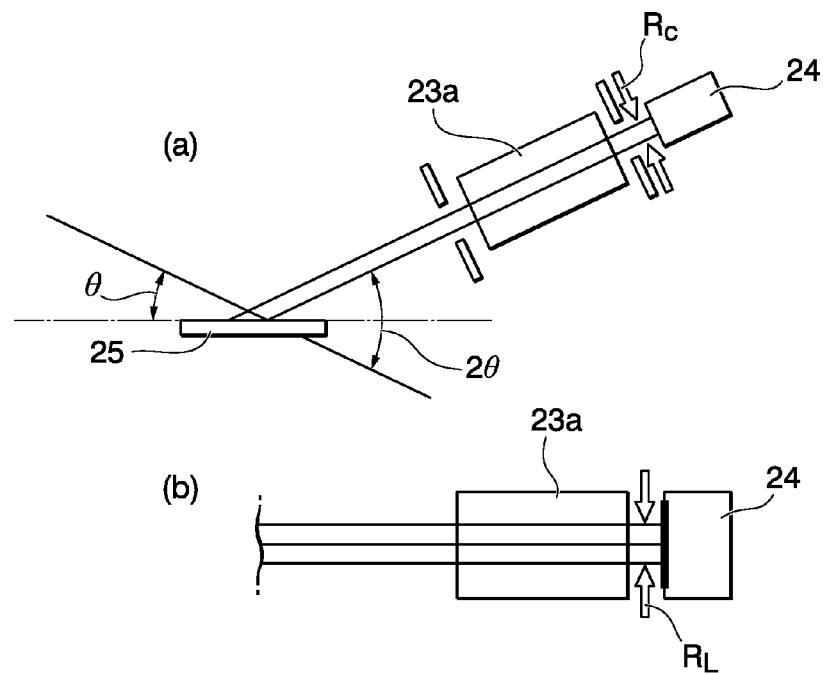
FIG. 4 is a view of the arrangement of an optical system on a light-receiving side, in which (a) is a side view, and (b) is a view of a beam surface.

Next, the light-receiving optical system 23 will be described. An example of the arrangement of the light-receiving optical system is shown in FIG. 4. FIG. 4 shows an example in which the solar slit 23a is used as the optical element, in which (a) in FIG. 4 is a side view of the sample viewed from the side, and (b) in FIG. 4 is a view of a beam surface viewed vertically from above the sample (view of beam surface). The role of the solar slit 23a in the light-receiving optical system 23 is to enhance resolution. The principle is as shown above in FIG. 5. The product of a beam width $R_c$ of the X-ray beam incident on the detector 24 and a beam height $R_L$ thereof becomes an effective area of the X-ray beam in the detector 24. In order to capture signals as much as possible even when the steel sheet position is changed, the wider the effective area is, the better it is.

Next, as the X-ray detector that can be used in the determination apparatus according to this embodiment, for example, there are a proportional counter (PC) which achieves ionization by X-rays using gas, a scintillation counter (SC) which achieves ionization using a solid light-emitting action, a solid state detector (SSD) which is operated using a semiconductor element, and the like. As the proportional counter, a gas flow type acounter, in which operation is performed while allowing gas to flow, and a sealed type sealed in a metal container can be used. As the solid state detector, an Si (Li) type detector which is used while being cooled by liquid nitrogen, a silicon drift detector which does not use liquid nitrogen due to electron cooling, and the like. The proportional counter rather than the scintillation counter, and the solid state detector rather than these counters has an excellent ability to discriminate (energy resolution) of X-ray incident on the detector. However, the solid state detector is expensive and it is difficult to manufacture a large element with this. Therefore, not many solid state detectors having a large effective area are on the market. The scintillation counter and the proportional counter are relatively cheap and can be relatively easily manufactured to have an appropriate size for diffracted X-ray analysis, which is appropriate even in this embodiment.

In a case where the sample is a galvanized steel sheet, when the energy of incident X-rays is higher than the excitation energy of Fe-Kα fluorescence X-rays of the steel sheet, the X-rays incident on the detector 24 include both the diffracted rays of the incident X-rays and fluorescence X-rays of iron. The fluorescence X-rays of iron are treated as noise components in the diffracted rays and reduce the accuracy of the obtained information regarding the X-rays. Here, when rays having a lower excitation energy than that of the Fe-Kα fluorescence X-rays, for example, Co-Kα rays are selected as the energy of X-rays, the generation of fluorescence X-rays of iron can be limited. As a result, the accuracy of the obtained X-ray information can be increased, which is appropriately for use as the determination apparatus according to this embodiment. However, in this case, Zn-Kα fluorescence X-rays are not excited, and thus are not compatible with an X-ray source of a Zn coating weight meter.

The determination apparatus according to this embodiment includes the X-ray tube and the optical system designed to allow the two parameters "emitted beam luminance" and "width-direction gain" to be higher than specific lower limits on the premise of the parallel beam optical system, and can detect a desired diffraction peak with good sensitivity. First, the "emitted beam luminance" will be described.

The "emitted beam luminance" is the luminance of X-rays per sample irradiation area. The calculation order is as follows.

1) An effective focal point luminance is obtained.
2) Capture correction and reflectance correction are performed.

3) The emitted beam luminance is obtained from the correction and the sample irradiation area.

The effective focal point luminance is a value obtained by dividing the X-ray output by the actual focal area. The actual focal area is obtained as follows from the actual focal size shown in FIG. 1.

a) In case of point extraction: ½ (actual focal width)×½ (actual focal length)×π (5)

b) In case of line extraction: actual focal width× actual focal length (6)

A value that approaches an actual measurement value is obtained through calculation using elliptic approximation of the actual focal point in the case of the point extraction and using rectangular approximation in the case of the line extraction.

Next, capture correction is performed in consideration that the amount of the X-ray output per actual focal point unit area captured in the width direction and in the longitudinal direction, and reflectance correction is performed in consideration of the degree of reflection of the mirror being used. The correction expressions are as follows.

Capture correction=effective focal point luminance× capture angle width direction×capture angle longitudinal direction (7)

Reflectance correction=capture correction×reflectance width direction×reflectance longitudinal direction (8)

The capture correction is to correct the degree of the effective focal point luminance (the intensity of all X-rays that diverge from the X-ray source) being used (the product of width and length). The reflectance correction is the product of the reflectances of the optical element in the width direction and in the longitudinal direction.

(8) A value obtained by dividing the corrected values obtained in Expression (8) by the sample irradiation area is the "emitted beam luminance". The sample irradiation area is the product of the sample irradiation width $S_c$ and the sample irradiation length $S_L$ shown in FIGS. 3A and 3B. As the emitted beam luminance is increased, the signal intensity of the diffracted rays is increased, and thus a diffraction peak having high sensitivity and excellent quantitativity is obtained.

Next, the "width-direction gain" will be described. The width-direction gain is calculated by the following expression.

Width-direction gain=capture angle width direction× reflectance width direction (9)

The width-direction gain is an index that, when the optical element such as the mirror is viewed from the X-ray source, indicates the degree of visibility of the element in the width direction and the degree of reflectance being used. An increase in the width-direction gain means effective use of the optical element, and the X-rays from the ray source are effectively captured, collimated, and reflected to be guided to irradiate the sample.

In the determination apparatus of this embodiment, the emitted beam luminance is preferably 20 W/mm$^2$ or higher, more preferably 50 W/mm$^2$ or higher, and even more preferably 80 W/mm$^2$ or higher. When the emitted beam luminance is 20 W/mm$^2$ or higher, the diffraction intensity can be increased, and thus time for determination can be significantly reduced.

In addition, the width-direction gain is preferably 0.15 or higher, more preferably 0.25 or higher, and even more preferably 0.35 or higher. When the width-direction gain is 0.15 or higher, the utility of the X-rays can be increased. Accordingly, the diffraction intensity can be increased, and thus time for determination can be significantly reduced.

When the determination apparatus according to this embodiment is installed in the galvannealed steel sheet manufacturing line, the range of the installation position is in a range from the completion of alloying to coiling. In addition, a change in sheet thickness and the effect of steel sheet vibrations need to be considered. Although described later in Examples, in terms of apparatus performance, there is no problem in measurement sensitivity as long as a change from the reference position of the sample is within ±3 mm. Typically, it is thought that the range of the change in the sheet thickness is about 3 mm. Therefore, it is preferable that the determination apparatus is installed at a location in which the range of the steel sheet vibrations is controlled to be within 3 mm. As a method of controlling vibrations, well-known methods such as supporting using a touch roll, coiling around a roll, and installation of an anti-vibration device may be applied.

In this embodiment, the optical element that can be used in the optical system is exemplified by the solar slit and the multi-layer film parabolic mirror. However, the present invention is not limited thereto, and well-known optical elements such as a flat plate-type multi-layer film mirror having a flat reflective surface, and an analyzing crystal such as LiF, pyrographite, Si, or Ge may be applied. In addition, as in Example B, in a case where the analyzing crystal is used in the incidence optical system and the solar slit is also used thereafter, the sample irradiation width is obtained by using Expression (1), and the sample irradiation length is obtained by using Expression (4).

Hereinafter, a specific example of the determination apparatus according to this embodiment will be described with reference to FIG. 7.

As a representative example of an on-line measurement apparatus, the specific configuration of an apparatus for detecting a Γ·Γ$_1$ phase among Fe—Zn alloy phases will be described with reference to FIG. 7.

Figure 7:
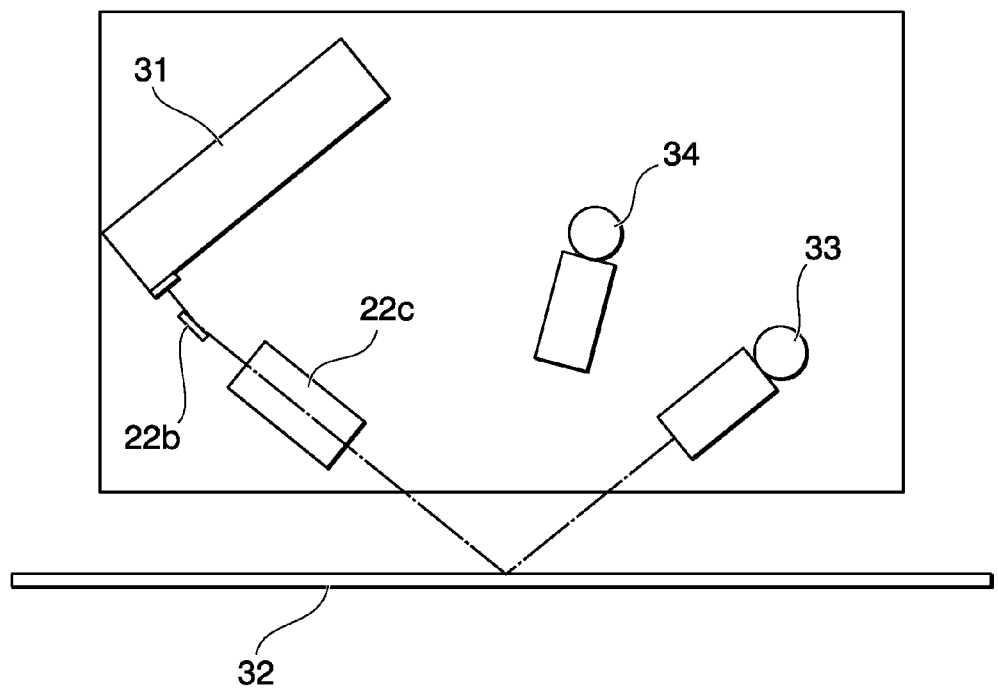
FIG. 7 is a schematic view showing an example of the on-line coating adhesion determination apparatus according to the present invention.

FIG. 7 is a schematic view of the on-line measurement apparatus for the Γ·Γ$_1$ phase in a case where a Co is used as the X-ray target. An extraction method of X-rays is the line extraction method. In FIG. 7, the slits, the count recording device, and the like is omitted. In the measurement apparatus, the diffraction angle 2θ of the X-rays is set to 55.86°. When a steel strip 32 is irradiated with the X-rays from an X-ray tube 31, a plurality of diffracted X-rays having different diffraction angles are generated. Among these, a detector 33 measures the intensity of the X-ray diffraction peak corresponding to a crystal lattice spacing d of 1.914 Å of the Γ·Γ$_1$ phase. A detector 34 measures the background intensity on the high angle side. The background measurement angle can be appropriately determined near the X-ray diffraction peak corresponding to d=1.914 Å detected by the detector 33 on the basis of the X-ray diffraction pattern, and for example, a measurement angle separated from the focused diffracted X-ray by about 0.5° to 15° may be employed. In practice, it is preferable that an appropriate background measurement angle for the background is obtained off-line prior to the on-line measurement. In addition, in a case where the difference in angle between the diffracted X-ray and the background is 5° or less, it is physically difficult to dispose the detector 34. Therefore, the background intensity may also be obtained by scanning only a predetermined angle near the diffraction angle using the detector 33 for the diffracted X-ray.

By using the above-described diffracted X-ray intensity, the amount of the Γ·Γ$_1$ phase can be measured. Regarding the quantification of the Γ·Γ$_1$ phase, a value obtained by subtracting the background intensity from the diffracted X-ray intensity may be configured into the amount of the phase on the basis of a calibration curve created in advance.

Figure 8:
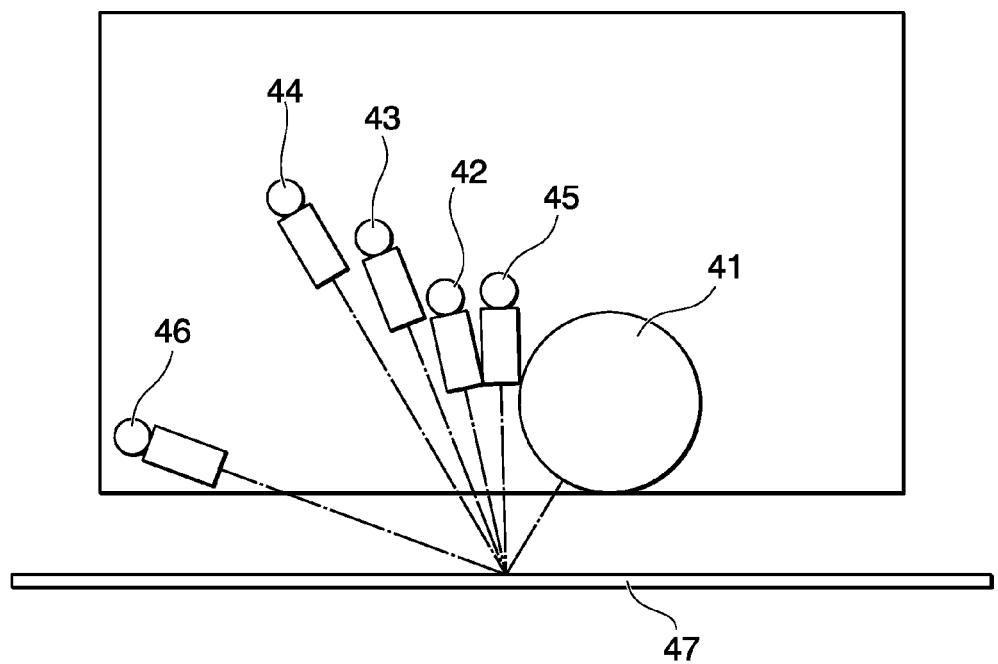
FIG. 8 is a schematic view showing an on-line coating adhesion determination apparatus according to the related art.

For comparison, the configuration of a high-angle-side Fe—Zn phase peak measurement apparatus according to the related art is shown in FIG. 8.

A determination apparatus shown in FIG. 8 is an on-line measurement apparatus for simultaneously measuring diffracted X-rays of two phases or three phases among the Γ·Γ$_1$ phase, the δ$_1$ phase, the ζ phases contained in the Fe—Zn alloy phases. In the figure, reference numeral 41 denotes a fluorescence X-ray tube which uses Cr as the target. Reference numeral 47 denotes a steel strip. A X-ray diffraction peaks corresponding to d=1.222 Å of the Γ·Γ$_1$ phase is detected by a detector 42, a X-ray diffraction peak corresponding to d=1.260 Å of the ζ phase is detected by a detector 43, and a X-ray diffraction peak corresponding to d=1.279 Å of the δ$_1$ phase is detected by a detector 44. In addition, a detector 45 measures a high-angle-side background intensity, and a detector 46 measures a low-angle-side background intensity.

As described above, according to the determination apparatus of this embodiment, the optical system which irradiates the galvannealed steel sheet with a parallel beam of the X-rays is provided as the optical system. Therefore, even when the galvannealed steel sheet which travels in a transportation line vibrates, the incident angle of the X-rays becomes constant in the beam, and thus the X-ray diffraction angle can be allowed to be constant, thereby enhancing the detection sensitivity of the diffracted X-rays. In addition, since the emitted beam luminance is 20 W/mm$^2$ or higher and the width-direction gain is 0.15 or higher, the X-ray diffraction intensity can be increased, and thus time for determination can be significantly reduced.

In addition, according to the determination apparatus of this embodiment, since the detector 24 is installed at a position of the diffraction angle at which the X-ray diffraction peak corresponding to a crystal lattice spacing d of 1.914 Å is detected, the thickness of the Γ·Γ$_1$ phase can be measured with good accuracy, and thus the adhesion of the coating layer can be determined with good accuracy.

Furthermore, according to the determination apparatus of this embodiment, since the X-ray tube in which the energy of the X-rays incident on the galvannealed steel sheet is lower than the excitation energy of Fe-Kα fluorescence X-rays is used as the X-ray tube, the detection sensitivity of the three phases of the Γ·Γ$_1$ phase, the δ$_1$ phase, and the ζ phase contained in the Fe—Zn alloy phases can be enhanced.

In addition, according to the manufacturing line of this embodiment, since the determination apparatus having shortened determination time is installed at a position at which the sum of a sheet thickness change and steel sheet vibrations is within ±3 mm between an alloying furnace and coiling. Therefore, even in a case where the sheet threading speed of the galvannealed steel sheet is increased, a necessary steel sheet length for adhesion determination can be reduced. Therefore, quality assurance on the entire length of the coil becomes possible, and rapid feedback to the operational conditions is facilitated.

EXAMPLES

Next, the present invention will be described using Examples.

In Example 1, results of measurement regarding a change in the intensity of an Fe—Zn phase low-angle peak corresponding to a crystal lattice spacing d of 1.5 Å or higher with the specifications of the X-ray tube and the optical system designed to change the "emitted beam luminance" and the "width-direction gain" using the parallel beam optical system in a laboratory are described. In Example 2, results of on-line measurement performed by installing the determination apparatus according to this embodiment in a galvanneal manufacturing line will be described. In addition, the present invention is not limited to the following examples.

Example 1

A sample of the galvannealed steel sheet manufactured in an actual line as a test steel sheet was prepared. The Zn coating weight was 45 g/m$^2$, and Fe (%) in the coating layer was 9.5% and 10.5%. Regarding determination of coating adhesion performed off-line, 9.5% was evaluated as pass (A grade), and 10.5% was evaluated as fail (C grade) although it was close to the borderline of pass and fail. Using this, measurement of the grades shown in Tables 3A to 3D was performed in the laboratory.

As the X-ray tube, fluorescence and diffraction sealed-type X-ray tubes which had varying output, focal size, and extraction method, and used Cr, Cu, and Co as metal targets were used. All of the extraction angles in the diffraction X-ray tube were 6°. As the fluorescence X-ray tube, an X-ray tube having a focal size on the target of 7 mm×7.5 mm and a target inclination angle of 26° with respect to electron beams from the filament was used. In this case, the effective focal size of the extracted X-rays became 7 mm×7 mm.

As the optical element of the incidence optical system, the following combinations were used. The combinations of the optical element are described along with symbols in Table 3B.

"-" . . . Only solar slit
"A" . . . Solar slit and multi-layer film parabolic mirror
"B" . . . Solar slit and pyrographite
"C" . . . Solar slit and flat type multi-layer film mirror As the optical element of the light-receiving optical system, the solar slit was used. As the detector, the following was used. The types of detectors are described along with symbols in Table 3B.

"S-PC" . . . Sealed type gas proportional counter
"SDD" . . . Solid state detector
"SC" . . . Scintillation counter The obtained diffraction signals of the Fe—Zn phase were evaluated from the following viewpoints.

Strength (Cps):

A value obtained by subtracting the background intensity from the peak intensity was obtained as the intensity using a steel sheet in which Fe (%) in the coating layer was 9.5%. The background was set to a straight line connecting both ends of the peak. The measurement time was 0.1 sec.

Determination Time (Sec):

The intensities of the steel sheet in which Fe (%) in the coating layer was 9.5% and a steel sheet in which Fe (%) was 10.5% were compared, and measurement time necessary for allowing the difference therebetween to become three times the measurement errors (theoretical standard deviation) was obtained. In a case of measuring the peak intensity of a Γ phase, the determination time corresponds to measurement time necessary for determination of pass or fail of adhesion.

Figure 10:
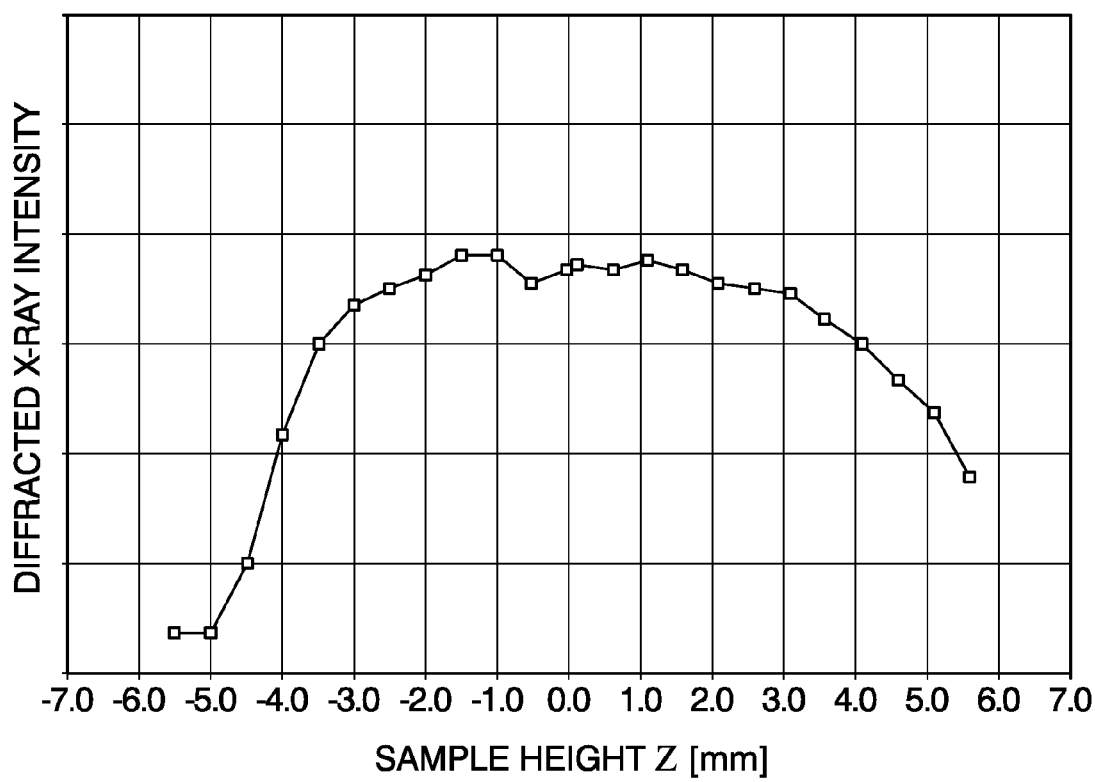
FIG. 10 is a graph showing the effect of steel sheet vibrations in the on-line coating adhesion determination apparatus according to the embodiment of the present invention.

Vibration Acceptability (Mm):

By using the steel sheet in which Fe (%) in the coating layer was 9.5%, a change in the peak intensity was examined while changing the sample position, and an acceptable degree of displacement due to vibrations was evaluated. An example of results is shown in FIG. 10. In this case, it is determined that vibrations of ±3 mm can be acceptable.

Figure 9:
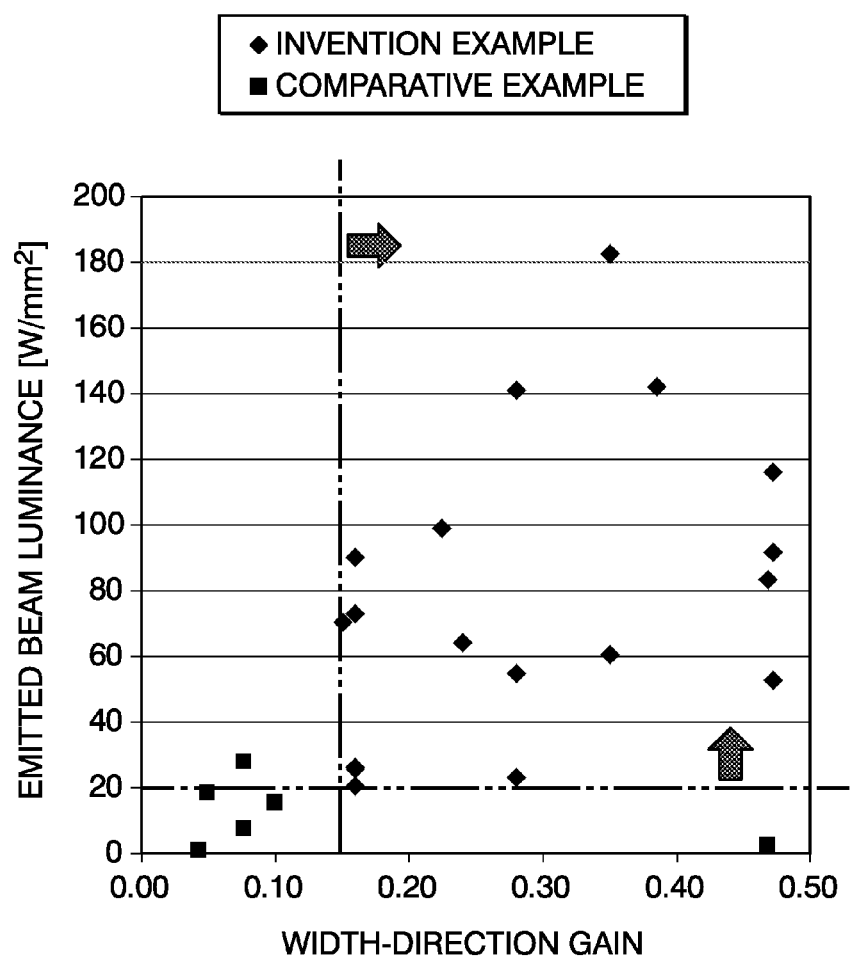
FIG. 9 is a view showing the relationship between an emitted beam luminance and a width-direction gain in the on-line coating adhesion determination apparatus according to the embodiment of the present invention, and is a graph for comparison between Invention Examples and Comparative Examples.

The results are shown in Tables 3A to 3D. In Nos. 1 to 28, the specifications of the X-ray tube and the optical system in Invention Examples were designed to increase the emitted beam luminance and the width-direction gain compared to Comparative Examples. The relationship is shown in FIG. 9. Here, when signal characteristics of Table 3 are compared to each other, compared to Comparative Examples, in Invention Examples, the signal intensity is high, the determination time is short, and an acceptable degree of vibrations is ±3 mm. As a result, the measurement time for high-speed sheet threading is reduced, and measurement can be performed without problems even when vibrations become intense. That is, followability for high-speed operations is high.

Nos. 29 to 31 are measurement examples of the high-angle-side Fe—Zn phase peak according to the related art. Although the signal intensity is high and steel sheet vibrations are acceptable, there is an original problem of peak separation of each phase, and the difference between samples having different Fe (%) in the coating layers cannot be accurately determined

TABLE 3A

X-ray tube specifications

| No | Ray source | Type | Output kW | Focal size (mm) Width | Focal size (mm) Length | Extraction method (*1) | Actual focal size (mm) Width | Actual focal size (mm) Length | Effective focal point luminance W/mm² |
|---|---|---|---|---|---|---|---|---|---|
| 1 | Cr | Diffraction | 2 | 2 | 12 | Point | 2 | 1.2 | 1061 |
| 2 | Cu | Diffraction | 1.5 | 0.4 | 8 | Point | 0.4 | 0.8 | 5968 |
| 3 | Co | Diffraction | 1.2 | 0.4 | 8 | Point | 0.4 | 0.8 | 4775 |
| 4 | Co | Diffraction | 1.8 | 1 | 10 | Line | 0.1 | 10 | 1800 |
| 5 | Co | Diffraction | 1.6 | 1 | 10 | Line | 0.1 | 10 | 1600 |
| 6 | Co | Diffraction | 1.8 | 1 | 10 | Line | 0.1 | 10 | 1800 |
| 7 | Cu | Diffraction | 1.6 | 1 | 10 | Line | 0.1 | 10 | 1600 |
| 8 | Cu | Diffraction | 1.5 | 0.4 | 8 | Point | 0.4 | 0.8 | 5968 |
| 9 | Co | Diffraction | 1.8 | 1 | 10 | Line | 0.1 | 10 | 1800 |
| 10 | Cr | Diffraction | 2.7 | 2 | 12 | Line | 0.2 | 12 | 1125 |
| 11 | Co | Diffraction | 1.8 | 1 | 10 | Line | 0.1 | 10 | 1800 |
| 12 | Co | Diffraction | 1.8 | 1 | 10 | Point | 1 | 1 | 2292 |
| 13 | Co | Diffraction | 1.2 | 0.4 | 8 | Point | 0.4 | 0.8 | 4775 |
| 14 | Cr | Diffraction | 1.3 | 0.4 | 8 | Point | 0.4 | 0.8 | 5173 |
| 15 | Co | Diffraction | 2.7 | 2 | 12 | Point | 2 | 1.2 | 1432 |
| 20 | Cr | Fluorescence | 2.8 | 7 | 7.5 | — | 7 | 7 | 57 |
| 21 | Co | Diffraction | 1.8 | 1 | 10 | Line | 0.1 | 10 | 1800 |
| 22 | Cr | Fluorescence | 2.8 | 7 | 7.5 | — | 7 | 7 | 57 |
| 23 | Cr | Diffraction | 2.7 | 2 | 12 | Point | 2 | 1.2 | 1432 |
| 24 | Co | Diffraction | 1.8 | 1 | 10 | Line | 0.1 | 10 | 1800 |
| 25 | Cu | Diffraction | 1.5 | 0.4 | 8 | Point | 0.4 | 0.8 | 5968 |
| 26 | Cr | Diffraction | 1.2 | 0.4 | 8 | Point | 0.4 | 0.8 | 4775 |
| 27 | Co | Diffraction | 1.2 | 0.4 | 8 | Point | 0.4 | 0.8 | 4775 |
| 28 | Cu | Diffraction | 1.2 | 0.4 | 8 | Point | 0.4 | 0.8 | 4775 |
| 29 | Cr | Fluorescence | 2.8 | 7 | 7.5 | — | 7 | 7 | 57 |
| 30 | Cr | Fluorescence | 2.8 | 7 | 7.5 | — | 7 | 7 | 57 |
| 31 | Cr | Fluorescence | 2.8 | 7 | 7.5 | — | 7 | 7 | 57 |

(*1) Extraction angle 6°

TABLE 3B

Optical system specifications

| No | Analyzing element (*2) | Capture angle (°) Width | Capture angle (°) Length | Reflectance (—) Width | Reflectance (—) Length | Emitted beam width mm | Sample incident angle ° | Restriction slit mm | Gonioradius mm | Sample distance (*3) mm |
|---|---|---|---|---|---|---|---|---|---|---|
| 1 | — | 0.15 | 7 | 0.5 | 1 | 1.2 | 36.65 | — | 250 | 100 |
| 2 | — | 0.15 | 7 | 0.5 | 1 | 1.2 | 23.5 | — | 250 | 100 |
| 3 | — | 0.10 | 7 | 0.5 | 1 | 1.2 | 27.9 | — | 250 | 100 |
| 4 | A | 0.67 | 5 | 0.7 | 1 | 1.13 | 29.5 | 10 | 250 | 100 |
| 5 | A | 0.50 | 5 | 0.7 | 1 | 1.13 | 29.5 | 10 | 250 | 100 |
| 6 | A | 0.67 | 5 | 0.7 | 1 | 1.13 | 29.5 | 10 | 200 | 60 |
| 7 | A | 0.67 | 5 | 0.7 | 1 | 1.13 | 23.5 | 10 | 200 | 60 |
| 8 | A | 0.50 | 5 | 0.7 | 1 | 1.13 | 23.5 | 10 | 250 | 100 |
| 9 | B | 0.40 | 4 | 0.4 | 1 | 1.13 | 29.5 | 10 | 200 | 60 |
| 10 | B | 0.40 | 6 | 0.4 | 1 | 1.13 | 36.65 | 10 | 200 | 60 |
| 11 | A | 0.40 | 5 | 0.7 | 1 | 1.13 | 29.5 | 10 | 250 | 100 |
| 12 | — | 0.40 | 4 | 0.6 | 1 | 1.13 | 29.5 | — | 150 | 50 |

TABLE 3B-continued

| | | Optical system specifications | | | | | | | | |
|---|---|---|---|---|---|---|---|---|---|---|
| | Analyzing | Capture angle (°) | | Reflectance (—) | | Emitted beam width | Sample incident angle | Restriction slit | Gonioradius | Sample distance (*3) |
| No | element (*2) | Width | Length | Width | Length | mm | ° | mm | mm | mm |
| 13 | — | 0.25 | 4 | 0.6 | 1 | 1.1 | 29.5 | — | 200 | 60 |
| 14 | B | 0.40 | 4 | 0.4 | 1 | 1.13 | 36.65 | 10 | 200 | 60 |
| 15 | B | 0.40 | 4 | 0.4 | 1 | 1.13 | 29.5 | 10 | 200 | 60 |
| 20 | C | 0.07 | 5 | 0.6 | 1 | 1.13 | 60 | 10 | 250 | 100 |
| 21 | B | 0.25 | 5 | 0.4 | 1 | 1.13 | 29.5 | 10 | 250 | 100 |
| 22 | A | 0.67 | 5 | 0.7 | 1 | 1.13 | 23.5 | 10 | 250 | 100 |
| 23 | A | 0.67 | 5 | 0.7 | 1 | 1.13 | 16.2 | 10 | 200 | 60 |
| 24 | — | 0.40 | 5 | 0.7 | 1 | 1.1 | 22.3 | — | 200 | 60 |
| 25 | B | 0.40 | 4 | 0.4 | 1 | 1.13 | 24.85 | 10 | 200 | 60 |
| 26 | A | 0.55 | 5 | 0.7 | 1 | 1.13 | 16.2 | 10 | 200 | 60 |
| 27 | A | 0.40 | 5 | 0.7 | 1 | 1.13 | 22.3 | 10 | 200 | 60 |
| 28 | A | 0.45 | 5 | 0.5 | 1 | 1.13 | 24.85 | 10 | 250 | 100 |
| 29 | — | 0.15 | 7 | 0.5 | 1 | 1.2 | 65.33 | — | 250 | 60 |
| 30 | — | 0.15 | 7 | 0.5 | 1 | 1.2 | 63.54 | — | 250 | 60 |
| 31 | — | 0.15 | 7 | 0.5 | 1 | 1.2 | 69.55 | — | 250 | 60 |

(*2) A: multi-layer film mirror (parabolic surface shape), B: graphite, C: multi-layer film mirror (flat surface shape)
(*3) Distance L between slit and sample

TABLE 3C

| | Beam efficiency index | | | | |
|---|---|---|---|---|---|
| No | Width-direction gain | Width · length of X-ray irradiation of sample (mm) | | Focal point luminance corrected value | Emitted beam luminance |
| | — | Width | Length | W/mm² | W/mm² |
| 1 | 0.077 | 2.46 | 31.90 | 568 | 7.25 |
| 2 | 0.077 | 3.68 | 31.50 | 3196 | 27.58 |
| 3 | 0.050 | 2.94 | 31.50 | 1671 | 18.06 |
| 4 | 0.472 | 2.47 | 18.75 | 4246 | 91.62 |
| 5 | 0.350 | 2.47 | 18.75 | 2800 | 60.41 |
| 6 | 0.472 | 2.40 | 15.25 | 4246 | 115.97 |
| 7 | 0.469 | 2.97 | 15.25 | 3752 | 82.98 |
| 8 | 0.350 | 3.05 | 18.75 | 10445 | 182.49 |
| 9 | 0.160 | 3.15 | 14.20 | 1152 | 25.80 |
| 10 | 0.160 | 2.59 | 16.31 | 1080 | 25.53 |
| 11 | 0.280 | 2.47 | 18.75 | 2520 | 54.37 |
| 12 | 0.240 | 3.00 | 11.49 | 2200 | 63.76 |
| 13 | 0.150 | 2.77 | 14.79 | 2865 | 70.06 |
| 14 | 0.160 | 2.59 | 14.20 | 3310 | 89.87 |
| 15 | 0.160 | 3.15 | 14.20 | 917 | 20.53 |
| 20 | 0.043 | 1.41 | 18.75 | 12 | 0.46 |
| 21 | 0.100 | 3.18 | 18.75 | 900 | 15.09 |
| 22 | 0.469 | 3.05 | 18.75 | 134 | 2.34 |
| 23 | 0.472 | 4.24 | 15.25 | 3379 | 52.29 |
| 24 | 0.280 | 4.00 | 27.50 | 2520 | 22.89 |
| 25 | 0.160 | 3.69 | 14.20 | 3820 | 73.01 |
| 26 | 0.385 | 4.24 | 15.25 | 9191 | 142.22 |
| 27 | 0.280 | 3.12 | 15.25 | 6685 | 140.68 |
| 28 | 0.225 | 2.90 | 18.75 | 5371 | 98.91 |
| 29 | 0.077 | 1.50 | 37.70 | 31 | 0.54 |
| 30 | 0.077 | 1.52 | 37.70 | 31 | 0.53 |
| 31 | 0.077 | 1.45 | 37.70 | 31 | 0.56 |

TABLE 3D

| | | Detector specifications | | | | Signal characteristics | | | |
|---|---|---|---|---|---|---|---|---|---|
| No | Detector | Effective area mm² | Diffraction angle ° | d value Å | Alloy phase — | Intensity cps | Measurement time sec | Vibration mm | Remark |
| 1 | S-PC | 100 | 73.3 | 1.914 | Γ | 0 | — | — | Comparative Example |
| 2 | SDD | 50 | 47.3 | 1.914 | Γ | 20 | 100 | ±1 | Comparative Example |
| 3 | S-PC | 100 | 55.8 | 1.914 | Γ | 0 | — | — | Comparative Example |
| 4 | SC | 100 | 55.8 | 1.914 | Γ | 2000 | 5 | ±3 | Invention Example |
| 5 | SC | 100 | 55.8 | 1.914 | Γ | 1200 | 8 | ±3 | Invention Example |
| 6 | S-PC | 100 | 55.8 | 1.914 | Γ | 2700 | 3 | ±3 | Invention Example |
| 7 | S-PC | 100 | 47.3 | 1.914 | Γ | 1850 | 14 | ±3 | Invention Example |
| 8 | SC | 100 | 47.3 | 1.914 | Γ | 2400 | 12 | ±3 | Invention Example |

TABLE 3D-continued

| | Detector specifications | | | | Signal characteristics | | | |
|---|---|---|---|---|---|---|---|---|
| No | Detector | Effective area mm² | Diffraction angle ° | d value Å | Alloy phase — | Intensity cps | Measurement time sec | Vibration mm | Remark |
| 9 | S-PC | 100 | 55.8 | 1.914 | Γ | 120 | 25 | ±3 | Invention Example |
| 10 | SC | 100 | 73.3 | 1.914 | Γ | 90 | 45 | ±3 | Invention Example |
| 11 | SC | 100 | 55.8 | 1.914 | Γ | 900 | 9 | ±3 | Invention Example |
| 12 | SC | 100 | 55.8 | 1.914 | Γ | 500 | 13 | ±3 | Invention Example |
| 13 | S-PC | 100 | 55.8 | 1.914 | Γ | 440 | 15 | ±3 | Invention Example |
| 14 | SC | 100 | 73.5 | 1.914 | Γ | 540 | 22 | ±3 | Invention Example |
| 15 | S-PC | 100 | 55.8 | 1.914 | Γ | 90 | 30 | ±3 | Invention Example |
| 20 | SC | 100 | 139.0 | 1.22 | Γ | 0 | — | — | Comparative Example |
| 21 | SC | 100 | 55.8 | 1.914 | Γ | 0 | — | — | Comparative Example |
| 22 | S-PC | 100 | 47.3 | 1.914 | Γ | 30 | 90 | ±3 | Comparative Example |
| 23 | S-PC | 100 | 32.4 | 4.109 | ζ | 1500 | 16 | ±3 | Invention Example |
| 24 | S-PC | 100 | 44.6 | 2.363 | δ | 380 | 17 | ±3 | Invention Example |
| 25 | S-PC | 100 | 49.7 | 1.833 | Γ | 370 | 35 | ±3 | Invention Example |
| 26 | S-PC | 100 | 32.4 | 4.109 | ζ | 2700 | 10 | ±3 | Invention Example |
| 27 | S-PC | 100 | 44.6 | 2.363 | δ | 2000 | 3 | ±3 | Invention Example |
| 28 | S-PC | 100 | 49.7 | 1.833 | Γ | 1400 | 18 | ±3 | Invention Example |
| 29 | S-PC | 100 | 130.7 | 1.26 | ζ | 1200 | (*4) | ±3 | Comparative Example |
| 30 | S-PC | 100 | 127.1 | 1.279 | δ | 900 | (*4) | ±3 | Comparative Example |
| 31 | S-PC | 100 | 139.1 | 1.222 | Γ | 300 | (*4) | ±3 | Comparative Example |

(*4) High-angle peak has high intensity but has deteriorated S/N.

Example 2

The determination apparatus according to this embodiment was installed in the galvannealed steel sheet manufacturing line. The installation position is a horizontal pass after the completion of alloying and a roll coiling section. The configuration of the apparatus is as shown in FIG. 7. The specifications of the apparatuses are as shown in No. 6 of Table 3.

The galvannealed steel sheet was manufactured in the manufacturing line at a line speed of 180 mpm. During the manufacturing of the galvannealed steel sheet, an alloying temperature was intentionally changed from an appropriate alloying temperature to an excessive alloying temperature to cause a good adhesion portion and a defective portion to be present in a single coil. This test was repeatedly conducted on three coils. Samples were obtained from a front portion, a middle portion, and a tail portion in the coils, and an off-line adhesion test was conducted. The grades of adhesion include an A grade (pass), a B grade (pass although the grade is close to the borderline of pass and fail), and a C grade (fail although the grade is close to the borderline of pass and fail). The samples were subjected to a constant potential electrolysis method to peel the coating layers and allow only a Γ phase single layer to remain, and the diffracted ray intensity of the Γ phase was obtained off-line.

On the other hand, during the manufacturing of the coils, by operating the determination apparatus according to this embodiment shown in FIG. 7, the diffracted ray intensity of the Γ phase was measured on-line. The results are shown in FIG. 11 in which this is plotted by the vertical axis and the diffracted ray intensity of the Γ phase single layer obtained off-line is plotted by the horizontal axis.

Figure 11:
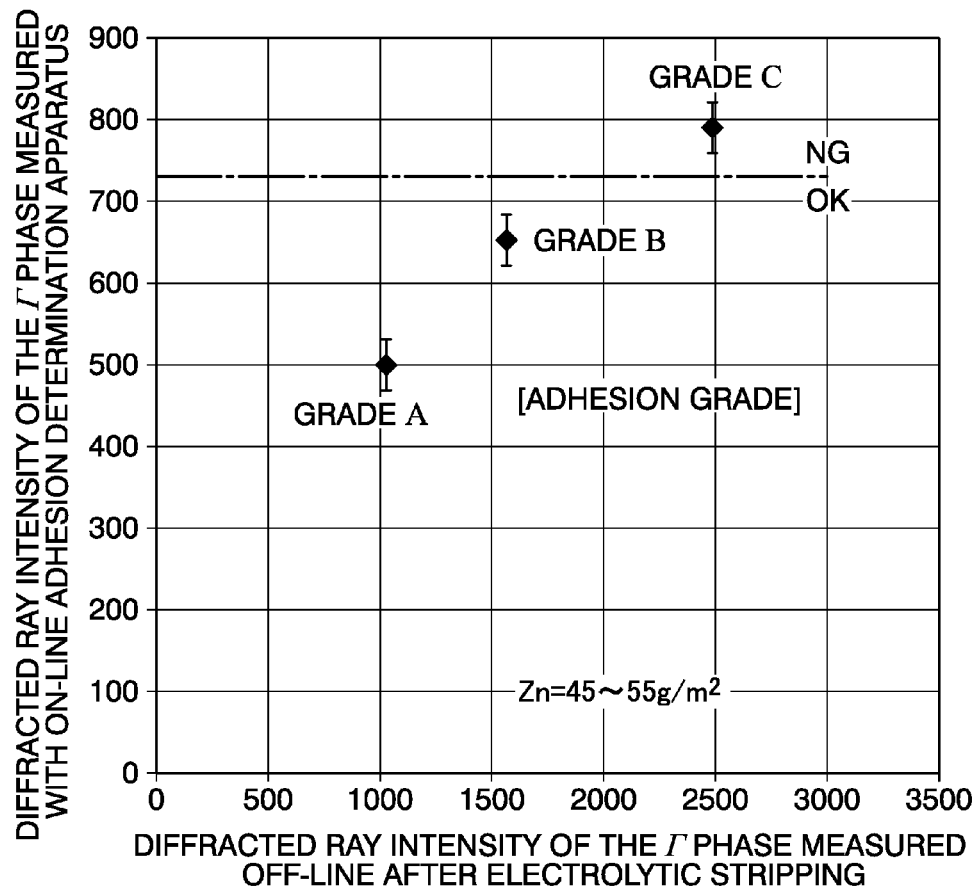
FIG. 11 show results of examination on the relationship between a Γ phase diffracted ray intensity measured by the on-line coating adhesion determination apparatus according to the present invention, and off-line coating adhesion test results.

It can be seen from FIG. 11 that even in a case where the galvannealed steel sheet is subjected to a high-speed operation at a line speed of 180 mpm, the determination apparatus according to this embodiment can accurately determine coating adhesion similarly to off-line evaluation.

While the preferable embodiments of the present invention have been described in detail with reference to the drawings, the present invention is not limited to the embodiments. It should be noted by those skilled in the art to which the present invention belongs that various changes and modification examples can be made in the scope of the technical spirit described in the appended claims, and these examples naturally belong to the technical range of the present invention.

INDUSTRIAL APPLICABILITY

According to the present invention, a galvannealed steel sheet with stable quality can be stably supplied at low cost, and thus the spread of vehicles with excellent antirust properties is further accelerated. This is connected to the enhancement in the life-span and safety of vehicles and contributes to the improvement in the global environment from the viewpoint of saving resources. Therefore, industrial utility is extremely high.

BRIEF DESCRIPTION OF THE REFERENCE SYMBOLS

21: X-RAY SOURCE (X-RAY TUBE)
22: INCIDENCE OPTICAL SYSTEM (OPTICAL SYSTEM)
24: DETECTOR

What is claimed is:

1. An on-line coating adhesion determination apparatus of a galvannealed steel sheet, comprising:
   an X-ray tube which irradiates a galvannealed steel sheet that travels on a transportation line, with X-rays;
   an optical system which allows the X-rays emitted from the X-ray tube to irradiate the galvannealed steel sheet as a parallel beam and be diffracted; and
   a detector which measures an intensity of the diffracted X-rays and is installed at a position at which a X-ray diffraction peak corresponding to a crystal lattice spacing d of 1.5 Å or higher is detected,
   wherein an emitted beam luminance of the X-rays is 20 W/mm2 or higher, and a width-direction gain of the X-rays in the optical system is 0.15 or higher.

2. The on-line coating adhesion determination apparatus of a galvannealed steel sheet according to claim 1,
   wherein the detector is installed at a position at which a X-ray diffraction peak corresponding to a crystal lattice spacing any one of d of 1.507 Å, 1.536 Å, 1.623 Å, 1.720 Å, 1.833 Å, 1.899 Å, 1.914 Å, 1.971 Å, 2.363 Å, 2.593 Å, 2.770 Å, 3.692 Å, 4.109 Å, 5.535 Å, or 6.351 Å is detected.

3. The on-line coating adhesion determination apparatus of a galvannealed steel sheet according to claim 1,
   wherein, as the X-ray tube, an X-ray tube in which an energy of the X-rays incident on the galvannealed steel sheet is lower than an excitation energy of Fe-Kα fluorescence X-rays, is used.

4. A galvannealed steel sheet manufacturing line comprising:
   the on-line coating adhesion determination apparatus according to claim 1 which is installed at a position at which a sum of a sheet thickness change and steel sheet vibrations is within ±3 mm between an alloying furnace and coiling.

5. The on-line coating adhesion determination apparatus of a galvannealed steel sheet according to claim 2,
   wherein, as the X-ray tube, an X-ray tube in which an energy of the X-rays incident on the galvannealed steel sheet is lower than an excitation energy of Fe-Kα fluorescence X-rays, is used.

6. A galvannealed steel sheet manufacturing line comprising:
   the on-line coating adhesion determination apparatus according to claim 2 which is installed at a position at which a sum of a sheet thickness change and steel sheet vibrations is within ±3 mm between an alloying furnace and coiling.

7. A galvannealed steel sheet manufacturing line comprising:
   the on-line coating adhesion determination apparatus according to claim 3 which is installed at a position at which a sum of a sheet thickness change and steel sheet vibrations is within ±3 mm between an alloying furnace and coiling.

* * * * *